United States Patent
Goble et al.

(10) Patent No.: US 6,758,846 B2
(45) Date of Patent: Jul. 6, 2004

(54) ELECTROSURGICAL INSTRUMENT AND AN ELECTROSURGERY SYSTEM INCLUDING SUCH AN INSTRUMENT

(75) Inventors: Colin C. O. Goble, Penarth (GB); Nigel M Goble, Castleton (GB)

(73) Assignee: Gyrus Medical Limited, Cardiff (GB)

( * ) Notice: Subject to any disclaimer, the term of this patent is extended or adjusted under 35 U.S.C. 154(b) by 165 days.

(21) Appl. No.: 09/773,893

(22) Filed: Feb. 2, 2001

(65) Prior Publication Data

US 2001/0014804 A1 Aug. 16, 2001

Related U.S. Application Data

(60) Provisional application No. 60/181,084, filed on Feb. 8, 2000.

(30) Foreign Application Priority Data

Feb. 8, 2000 (GB) .............................. 0002849

(51) Int. Cl.[7] .............................................. A61B 18/18
(52) U.S. Cl. .............................. 606/41; 606/34; 606/48; 606/50; 606/51; 606/49; 607/101; 607/104; 607/105
(58) Field of Search ............................. 606/41, 34, 48, 606/50, 51, 42, 32, 33, 45, 46, 47, 49, 35, 37, 38, 39, 40; 600/374; 604/21, 22, 114; 607/100, 101, 102, 103, 104, 105, 115, 116

(56) References Cited

U.S. PATENT DOCUMENTS

| | | | |
|---|---|---|---|
| 4,116,198 A | | 9/1978 | Roos |
| 4,674,499 A | * | 6/1987 | Pao .............................. 606/50 |
| 5,009,656 A | | 4/1991 | Reimels |
| 5,451,224 A | * | 9/1995 | Goble et al. ................... 606/48 |
| 6,004,319 A | * | 12/1999 | Goble et al. ................... 606/48 |
| 6,056,746 A | * | 5/2000 | Goble et al. ................... 606/48 |
| 6,090,106 A | * | 7/2000 | Goble et al. ................... 606/41 |
| 6,228,081 B1 | * | 5/2001 | Goble ......................... 606/34 |
| 6,306,134 B1 | * | 10/2001 | Goble et al. ................... 606/42 |
| 6,632,193 B1 | | 10/2003 | Davison et al. |

FOREIGN PATENT DOCUMENTS

| | | |
|---|---|---|
| GB | 2 308 979 | 7/1997 |
| GB | 2 308 980 | 7/1997 |
| GB | 2 308 981 | 7/1997 |
| WO | WO 99/49799 | 10/1999 |

\* cited by examiner

*Primary Examiner*—Henry Bennett
*Assistant Examiner*—Fadi H. Dahbour
(74) *Attorney, Agent, or Firm*—Nixon & Vanderhye P.C.

(57) ABSTRACT

In an electrosurgical system which is operable within the frequency range of from 100kHz to 50MHz and which has a handheld instrument with an elongate instrument shaft, the distal end of the shaft carries a bipolar electrode assembly for use in a conductive fluid field. The electrode assembly has an active electrode and, set back from the active electrode, a return electrode coated with an insulative dielectric layer. The insulative layer may be made of a plastics or a ceramic material and acts as the dielectric of a capacitor when the electrode assembly is immersed in the conductive fluid. One of the effects of the insulative layer is to provide a more uniformly distributed electric field over the return electrode than is obtained with an exposed return electrode, yielding improved tissue desiccation and vaporisation characteristics. The active electrode may have a similar dielectric covering.

40 Claims, 6 Drawing Sheets

Fig.5A COMMON MODE ISOLATION

Fig.5B ISOLATION TRANSFORMER

ELECTROSURGICAL INSTRUMENT AND AN ELECTROSURGERY SYSTEM INCLUDING SUCH AN INSTRUMENT

This application claims the benefit of U.S. Provisional Application No. 60/181,084, filed Feb. 8, 2000, the entire content of which is hereby incorporated by reference in this application.

FIELD OF THE INVENTION

This invention relates to an electrosurgical instrument and an electrosurgery system including the instrument and a radio frequency generator system for treatment of tissue, wherein the operative site and distal portion of such an instrument are immersed in an aqueous solution during use to vaporise, coagulate, desiccate or otherwise thermally modify such tissues.

BACKGROUND OF THE INVENTION

Electrosurgery has been used in surgical practice for over fifty years and during that time has seen a number of improvements to enhance safety and performance in more challenging surgical environments. One such challenge has been the emerging use of minimal access or endoscopic techniques to perform an ever increasing range of surgical procedures.

Traditional monopolar and bipolar electrosurgical devices have been widely used in endoscopic surgery but have suffered from a number of technical disadvantages, particularly when the operative site is distended or irrigated with aqueous solutions. Such solutions are commonly employed to improve endoscopic visualisation and are usually introduced to the body cavity through a specific channel provided in the endoscope itself. The immersion of electrosurgical instruments in aqueous solutions introduces a number of technical hurdles in terms of insulation and preventing power dissipation to the solution rather than the target site.

Monopolar electrosurgery requires the aqueous solution to be non-conductive in order to operate efficiently. Despite use of solutions such as Dextrose, Sorbitol and Glycine which have very low values of electrical conductance, tissue and bodily fluids released during the operation can significantly increase the conductance of fluids bathing the target site. This usually necessitates increasing power output to overcome losses to the solution in order to maintain performance. Increasing power output increases the recognised risk of inadvertent burns to the patient or operator when using monopolar arrangements.

Burns associated with monopolar arrangements can be avoided, albeit in an instrument with limited power, by use of capacitive coupling in a return path between tissue adjacent the operative site and the conductive casing of a self-contained battery-powered instrument such as that disclosed in the applicant's International Application No. WO97/15237. This device has a single exposed electrode and with an integral generator inside a metallic handheld casing and is intended for dry field use at high frequencies. The casing, acts as a conductor capacitively coupled to its surroundings to provide a capacitive return path from tissue being treated to the generator within the casing. The impedance of the return path is widely variable due to the varying degree to which the instrument is capacitively coupled to the surgeon's hand and the variable juxtaposition of surrounding conductive masses. A thin plastics coating is provided over the casing to prevent direct electrical contact with conductive masses.

While a conventional bipolar electrosurgical instrument, in which the two poles of the electrosurgical output are mounted as neighbouring electrodes on the tip of the instrument and both are required to contact tissue in order to produce an effect, to a large extent eliminate the risks of burns, the output power will still preferentially pass through conductive fluid present at the application site rather than the tissue itself. Nonetheless, the heating of such fluid can produce secondary heating of the tissue and thereby produce coagulation or desiccation of the tissue. The problem is much more evident when trying to use a bipolar arrangement to cut or ablate tissue whereby the solution lowers the impedance of the output and prevents the output voltage reaching the levels necessary to induce vaporisation of the tissue, typically requiring a peak-to-peak voltage in excess of 500V.

U.S. Pat. No. 5,009,656, Reimels, describes a method of overcoming this problem in which the two electrodes of a bipolar pair are brought sufficiently close, such that the gap between them supports the production of water vapour and direct arcing between the two electrodes. Although the technique provides for a method of arcing during immersion in conductive fluid, the gap is so small that the tissue effect is very limited.

U.S. Pat. No. 4,116,198, Roos, describes a further technique of overcoming some of the problems associated with use of bipolar arrangements when immersed in electrically conductive solutions. This technique overcomes the limitations of Reimels by use of a return electrode which is set back from the active electrode such that a more protracted electrical circuit is completed by the solution and direct arcing between the two is avoided. By this means only one electrode of the bipolar pair is required to contact tissue and the electric field is sufficient to include the tissue at the application site. This technique was successfully employed in endoscopic surgical procedures involving transuretheral resection of the prostate gland, as described by Elsasser and Roos in an article entitled 'Concerning an Instrument for Transuretheral Resection without Leakage of a Current', published in the German magazine 'Acta Medico Technica' 1976 vol. 24 No. 4 pages 129–134.

The present applicants' co-pending patent applications relating to electrosurgery describe further improvements over the Roos prior art to control the dimensions of the active electrode relative to a complex interaction between the configuration of the active electrode, the power threshold to establish arcing at the active electrode and control features in the electrosurgical generator component of the system. The commercial embodiments of these inventions are now widely used in the fields of arthroscopic, hysteroscopic and urological surgery.

U.S. Pat. Nos. 5,366,443 and 5,697,909 in the names of Eggers and Thapliyal describe an alternative approach using an array of active electrodes which can be selectively activated, or current limited, in order to reduce power dissipation into the electrically conductive fluid.

The above arrangements tend to suffer from a number of problems and technical limitations during use. Carbon tracking is a problem wherein the carbon residue derived from tissue vaporisation forms a conductive track between active and return electrodes. Once established, the track has a negative temperature co-efficient of resistance so that the hotter the carbon becomes, the more conductive it becomes and the more current flows along the track between the electrodes. The temperature developed in the track places huge thermal stresses on the insulator separating the return and active electrodes, which may result in catastrophic failure. Similar failures can occur due to overheating of the electrode assembly without carbon track formation when only portions of the distal tip assembly are in contact with fluid such that current can still flow in the absence of sufficient fluid cooling of the assembly.

In these prior devices, the electric field becomes concentrated in the region representing the shortest conduction path through the fluid medium. The shortest paths occur between the most distal portion of the return electrode and the most proximal region of the active electrode exposed to the fluid. The effects of this are two-fold: firstly, the high current density may cause the return electrode to become "active", particularly when the distal portion of the electrode is only partially immersed in fluid due to the accumulation of gaseous by-products produced during vaporisation; and, secondly, the depth of tissue effect is limited by the concentration of the electric field, particularly when a deeper coagulative effect is desirable.

When the active electrode is partially wetted and partially enveloped in vapour, very high powers are required to sustain what is, in effect, an unstable condition which usually results in intermittent collapse of the vapour pocket and variable surgical performance. The prior art describes certain ratios of the shortest and longest conduction path lengths between the active and return electrodes to reduce this effect. The effect is exacerbated by high fluid flows when the vapour pocket can become quenched, and, once again, high powers are required to overcome this quenching effect. Nevertheless, the surgical performance is variable. The prior art includes techniques to reduce this power threshold of vaporisation in the presence of a fluid flow, but the techniques involved impose some geometric limitations on the electrode assembly which can be difficult to implement in certain fields of application, particularly when active suction or fluid delivery occurs adjacent to, or through, the electrode itself.

It is an aim of this invention to provide an electrosurgical instrument for treating tissue immersed in a conductive fluid, which overcomes at least some of the disadvantages set out above.

SUMMARY OF THE INVENTION

According to a first aspect of this invention, there is provided an electrosurgical instrument for use at a frequency or frequencies in the range of from 100 kHz to 50 MHz, the instrument having a bipolar electrode assembly for tissue treatment when immersed in a conductive fluid, wherein the instrument comprises an elongate shaft mounted at one end to a handpiece, and carrying the electrode assembly at its other end, and wherein the electrode assembly comprises at least one distal active electrode, and an adjacent return electrode set back proximally of the active electrode, the return electrode being encased in an insulative dielectric layer. When the electrode assembly is immersed in a conductive fluid, the return electrode, due to having no exposed portion immersed in fluid, is capacitvely coupled to the fluid, the capacitance of the coupling depending on, inter alia, the thickness of the dielectric covering, its relative dielectric constant ($\epsilon_r$), and the area of the return electrode.

According to another aspect of the present invention, there is provided an electrosurgical system including a generator delivering a radio frequency output for the treatment of tissue structures in the high to very high frequency range. The generator is connected to an electrode assembly immersed in an electrically conductive fluid, the electrode assembly including an active zone and a return zone at the distal end, wherein one of either or both zones are insulated from direct electrical contact with either the tissue or the electrically conductive fluid such that, in use, the output circuit is completed by dielectric coupling through the insulation.

The invention also includes an electrosurgical instrument for wet field electrosurgery, wherein the instrument comprises a tubular elongate shaft for insertion into a body cavity and, at the end of the shaft for insertion into the body cavity, an electrode assembly comprising a first conductor at an extreme distal end of the instrument and a second conductor insulated from the first conductor and set back from the distal end, wherein at least the second conductor is encased in an insulative outer dielectric layer. An electrosurgery system including such an instrument may include a generator having a pair of output terminals coupled respectively to the first and second conductors of the electrode assembly, wherein the frequency of operation of the generator and the construction and materials of the second conductor and the encasing insulative layer are such that when a radio frequency current of 2 amps is delivered to the electrode assembly when immersed in normal saline, the current density at the outer surface if the insulative layer does not exceed 50 mA/mm$^2$.

According to another aspect of the invention, there is provided an electrosurgery system for treating tissue structure contained within a body cavity and immersed in an electrically conductive fluid, the system comprising: a generator for delivering a radio frequency output for the treatment of tissue structures in the high to very high frequency range; and an electrode assembly connected to the generator, the electrode assembly comprising: an active electrode including an active zone at a distal end of the active electrode; a return electrode including a return zone defined by an electric field developed between the active electrode and the return electrode when the electrode assembly is connected to the radio frequency output of the generator; and an insulator separating the return electrode from the active electrode; the return zone being coated with a layer of dielectric insulating material wherein, in use, the return zone is insulated from direct electrical contact with the tissue and the electrically conductive fluid so that an electrical circuit is completed between the active and return zones by dielectric coupling through the dielectric insulating material.

According to yet another aspect of the invention, there is provided an electrode assembly for treating a tissue structure contained within a body cavity and immersed in an electrically conductive fluid, the electrode assembly being connected to a generator for delivering a radio frequency output for the treatment of tissue structures in the high to very high frequency range, wherein the assembly comprises: an active electrode including an active zone at a distal end of the active electrode; a return electrode including a return zone defined by an electric field developed between the active electrode and the return electrode when electrode assembly is connected to the radio frequency output of the generator; and an insulator separating the return electrode from the active electrode; the return zone being coated with a dielectric insulating material layer wherein, in use, the return zone is insulated from direct electrical contact with the tissue and said electrically conductive fluid so that an electrical circuit is completed between the active and return zones by dielectric coupling through the dielectric insulating material. The active zone may be coated with a second dielectric insulating material layer so that the active zone is insulated from direct electrical contact with the tissue and the electrically conductive fluid and, in use, a circuit is completed between the active and return electrodes by dielectric coupling also through the second dielectric insulating material.

According to a further aspect, the invention also includes an electrode assembly for treating tissue structure contained within a body cavity and immersed in an electrically conductive fluid, the assembly being connected to a generator for delivering a radio frequency output to said electrode assembly, wherein the assembly comprises: an active electrode in the form of a ceramic body having an internal cavity lined with metal, the active electrode including an active zone at a distal end of the active electrode; and a return electrode including a return zone defined by an electric field developed between the active electrode and the return electrode when the electrode is connected to the radio frequency output of said generator; the ceramic body being made of a dielectric insulating material, wherein, in use, an electrical circuit is completed between the active and return zones by dielectric coupling. The radio frequency output advantageously interacts with the dielectric insulating material to result in a substantially uniformly distribution of the electric field over the return zone and a corresponding substantially uniform current density over the return zone. Preferably, the return zone is coated with a second dielectric insulating material, and the radio frequency output interacts with the dielectric insulating material and the second dielectric insulating material to result in a substantially uniformly distribution of the electric field over the active and return zones and a corresponding substantially uniform current density over those zones.

Features of other aspects of the invention and its preferred embodiments are set out in the claims.

The properties of the dielectric insulating material, coupled with variations in the electrosurgical output frequency and the combination of one or either or both of the active and return zones being coated in the dielectric material, enable manipulation of the electric field and current density created during use in order to confer significant performance advantages over prior art devices. These advantages can be realised in the electrodes geometrically configured to perform specific procedures on different tissue structures such as structures contained within cavities, lumens, ventricles or other natural body cavities containing an electrically conductive fluid, whether or not such fluid is naturally present or introduced as part of the surgical procedure. Such cavities may also be provided by artificial fluid enclosures or by surgical creation of the cavity. Of specific advantage, the performance of instruments in accordance with the invention can be made less susceptible to overheating and the effects of fluid flow on during use.

The invention will be described below in more detail by way of example.

BRIEF DESCRIPTION OF THE DRAWINGS

The accompanying drawings, which are incorporated in and form part of the specification, illustrate several embodiments of the invention and, together with the description, serve to explain the principles of the invention.

In the drawings.

Figure 1:
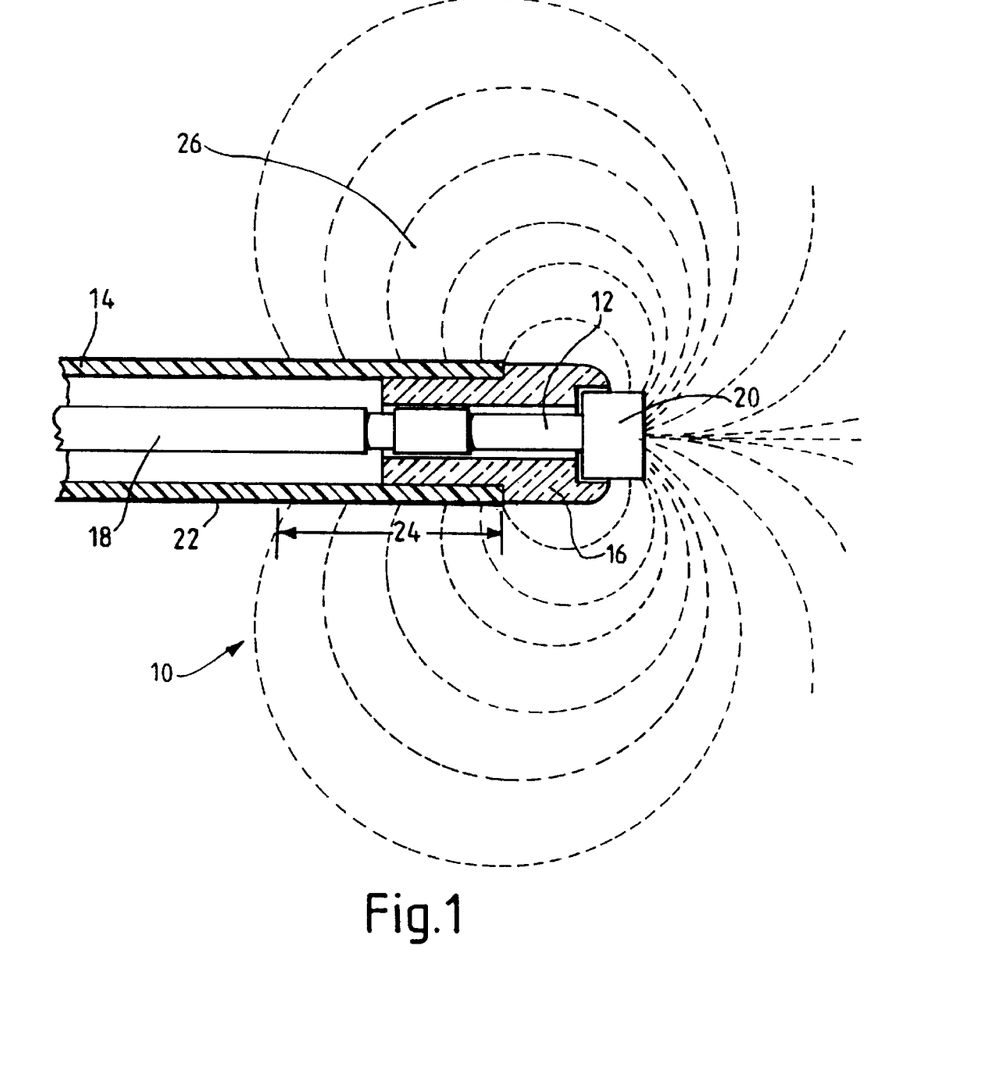
FIG. 1 is a partially sectioned side view of an electrode assembly of a first preferred embodiment of the invention.

Referring to FIG. 1, an electrode assembly 10 is located at the working end of a shaft of an instrument in accordance with the present invention, wherein the return path for the electrosurgical current passing through the electrode assembly is completed by dielectric coupling. The electrode assembly 10 is connected to a generator (not shown) providing a radio frequency output to the assembly in the range of from 100 kHz to 50 MHz. Electrode assembly 10 includes a metallic active electrode 12, a metallic return electrode 14, and a ceramic insulator 16 separating active electrode 12 from return electrode 14. Return electrode 14 is connected to the generator, as is active electrode 12, which is connected to the generator via an active conductor 18 that extends through the hollow centre return electrode 14. Active electrode 12 includes an active zone 20 at the distal end of electrode 12. Return electrode 14 is a metallic conductor, which serves as the shaft of the instrument, and which is covered by a thin plastics dielectric coating 22 over at least a distal end portion, the conductor being completely sealed from the outside. Return electrode 14 also includes a return zone 24 that is substantially at the distal end of electrode 14.

The dielectric material used for coating 22 in the embodiment of FIG. 1 preferably has a high relative dielectric constant (e.g. $\epsilon_r$ in excess of 2) and a low dielectric loss. One material for high frequency use (in excess of 5 MHz) is polyimide, which has an exceptional dielectric strength and can be coated in very thin layers. Its relative dielectric constant is 3.4. For example, a 50 $\mu$m coating of polyimide has sufficient dielectric strength to withstand the typical maximum output voltage of the generator to which electrode assembly 10 is connected. Such voltages may be in the region of 120Vrms for tissue coagulation and 200 to 500Vrms for tissue cutting and vaporisation. It should be noted, however, because the purpose of the dielectric coating is to capacitively couple energy to a conductive solution surrounding electrode 10, it is possible to use dielectric coatings that are thinner than 50 $\mu$m. For lower frequencies, materials with higher relative dielectric constants are preferred, suitable examples being titanium dioxide ($\epsilon_r$= 100) and barium titanate compounds (having $\epsilon_r$ values from 30 to as high as 1600).

The electrode assembly 10 shown in FIG. 1 is useful for illustrating the effect of use of a dielectric covering in accordance with the present invention. In the embodiment shown in FIG. 1, return electrode 14 has a diameter of 3.3 mm. Return zone 24 of return electrode 14 is associated with a distributed electric field pattern 26 that is developed between active electrode 12 and return electrode 14 when such electrodes are connected to the output of the generator to which electrode assembly 10 is attached. Return zone 24 is coated with polyimide dielectric coating 22, and typically extends a distance of at least 10 mm, preferably 20 mm along shaft 14 from the most distal end of the shaft when the active electrode 12 is not similarly coated. In this case, the overall area of the return zone is, therefore, about 200 mm².

Since polyimide has a relative dielectric constant $\epsilon_r$ of 3.4, the return coupling capacitance to the conductive solution surrounding the electrode assembly 10 is 125 pF with a 50 μm dielectric coating (or 250 pF with a 25 μm dielectric coating). At an electrosurgical output frequency of 1 MHz this represents an impedance of 1275Ω with a 50 μm dielectric coating or 638Ω with a 25 μm dielectric coupling. When the electrode assembly is immersed in a conductive solution, such as saline, the conductive path between the active zone 20 and the return zone 24 can have an impedance as low as 50Ω. At such a low impedance compared with that of the coating, very little power would be delivered. However, the impedance of the return coupling capacitance falls with increasing output frequency as shown in Table 1 below.

TABLE 1

| Frequency | 50 μm coating | 25 μm coating |
|---|---|---|
| 6.79 MHz | 188 Ω | 94 Ω |
| 13.56 MHz | 94 Ω | 47 Ω |
| 27.12 MHz | 47 Ω | 23 Ω |
| 40.68 MHz | 32 Ω | 16 Ω |

The above frequencies are in the internationally recognised Industrial Scientific or Medical bands (ISM). Clearly, there are coating thickness and output frequency options for which the majority of the applied voltage will appear across the load rather than the capacitance of dielectric coating 22. There are, however, considerable control implications related to the capacitive coupling effect since it applies to operating in at least two electrosurgical output modes; i.e., one producing tissue desiccation and the other selected levels of tissue vaporisation.

It follows from Table 1 that use of a dielectric coating having $\epsilon_r$ of the order of that of polyimide, and with the stated thicknesses, requires operation at a relatively high frequency if there is a direct conduction path through conductive fluid between the outer surface of the coating and the surface of the other electrode. In other words, such a coating, when both it and the other electrode are wetted with normal saline, requires delivery of electrosurgical power typically at a frequency of at least 5 MHz. It will be appreciated, however, that if the electrosurgical procedure involves vaporisation of a conductive liquid adjacent either surface, the frequency of operation may be switched to a much lower value once vaporisation has been established since the impedance represented by the path between the two surfaces then rises. Indeed, the impedance may rise by a factor of 20 when a vapour pocket is established, which means that the impedance represented by the coating at the lower frequency is much less significant.

This yields the important concept of a system involving a multiple electrode assembly with at least one electrode having a dielectric coating, and operating the system in an upper frequency range for tissue coagulation or desiccation (with the surfaces of the assembly wetted), and in a lower frequency range for tissue cutting or vaporisation (with at least one of the surfaces lying beneath a layer of vapour). To maintain the same ratio between the inter-electrode impedance and the coating impedance when the former rises by 20 times, the frequency may be lowered also by a factor of 20, typically of 1 MHz or lower.

When operation at lower electrosurgical frequencies with a wetted electrode assembly is required, e.g. less than 5 MHz down to about 100 kHz, the dielectric coating may be formed of one of the higher dielectric constant materials referred to above. These are ceramic materials and are, therefore, better suited to coating thicknesses greater than 50 μm, preferably 100 μm or higher, depending on the capacitance required and the dielectric constant of the material.

With a material having a relative dielectric constant of 100, forming a 20 mm long window around a cylindrical return conductor of 3.3 mm diameter and giving a capacitor plate area of about 200 mmsq, a 100 μm thick coating provides a capacitance of 1.8 nF. This yields the return coupling impedances shown in Table 2 below at different frequencies.

TABLE 2

| Frequency | 100 μm coating | 200 μm coating |
|---|---|---|
| 0.5 MHz | 180 Ω | 360 Ω |
| 1 MHz | 90 Ω | 180 Ω |
| 2 MHz | 45 Ω | 90 Ω |

With very high dielectric constants, thicker coatings can be used, to the extent that the electrode assembly in the region of the return zone can be made as a ceramic tube as the main structural member of the assembly, with a metallised internal face.

In certain other co-pending applications of the applicants relating to electrosurgical devices, considerable importance was attributed to peak applied voltage from which certain voltage thresholds could be derived for controlling the desiccation and vaporisation modes. In the present instruments, however, the capacitance of the coating appears as an impedance between the electrodes which increases the voltage seen at the return zone 24 during the higher current delivery used during desiccation. Knowledge of the impedance of the coating at any particular frequency of operation allows an effective peak voltage to be calculated, i.e. the voltage between the active electrode and the outer surface of the coating, providing the current can also be measured. Thus, the effective peak voltage is defined by the vectoral subtraction of the voltage drop across the coating from the voltage between the active and return electrodes.

Since the insulative coatings described herein behave in a capacitive manner, the highest voltage drop across them occurs when current is at a maximum. Maximum current corresponds to the largest possible wetted surface with the saline temperature close to 100° C. (Saline has a negative temperature co-efficient of resistance and, therefore, has highest electrical conductivity just below boiling.) This maximum current condition is normally reached during desiccation and normally exceeded for vaporisation. It is, in fact, desirable to control effective peak voltage at this point for maximum desiccation effect, since this also corresponds to maximum power delivery for any electrode configuration, or for any coating.

Depending on electrode configuration, it is possible for the load impedance to fall to very low values in the region of 50Ω. Values of load impedances in this region are more likely to occur with larger electrode configurations wherein the power threshold could be as high as 160 W (i.e., an electrode capable of absorbing 160 W, while fully wetted). Such an electrode could draw as much as 3.2 amps of current. In the highest impedance combination of Table 1 (6.79 MHz with a 50 μm coating), the impedance of the dielectric coating is 188Ω. The voltage across the coating would therefore be 602Vrms, or 1701V peak-to-peak, given that, at the identified output frequencies, the waveform would necessarily be sinusoidal. The dielectric strength of polyimide is 22 kV/mm. The 50 μm coating, therefore, offers a dielectric strength of 1100V or 2200V peak-to-peak. As the electrosurgical output frequency or area of the coating is increased, there is an improved margin due to the lowered impedance. Typical operating frequencies are the 27 MHz and 40 MHz values mentioned above. The coating is typically a cylinder having an axial length of 10 to 50 mm. A diameter of 3.3 mm yields a coating area in the range of from 100 to 520 sqmm.

At the higher voltage outputs used to establish and maintain a vaporisation mode, the same electrode example would have a load impedance of approximately 10–20 times that seen in the desiccation mode, i.e., 500 to 1000Ω. Once vaporisation is established, power requirements typically fall by 50% of the maximum wetted power demand for a given electrode. Thus, in the above example, maximum current would be in the region of 0.28 to 0.4 amps. The voltage drop across the coating therefore falls to 50V (6.79 MHz with 50 μm coating).

A significant feature of the coating 22 applied over return zone 24 is that power density is limited over the return surface. For example, consider the embodiment in FIG. 1 with an output frequency of 13.56 MHz and a 50 μm dielectric coating, with an applied power of 120 W and a load impedance of 50Ω resulting in an applied current of 1.55 A. The overall voltage drop across the dielectric return coating 22 is in the region of 145V. Next, consider the shortest conduction path between the active zone 20 and the return zone 24, which can be assumed to be similar to a typical value in prior art devices, such as that shown in FIG. 2. The prior art electrode assembly 30 shown in FIG. 2 includes a metallic active electrode 32, a metallic return electrode 34, and a ceramic insulator 36 separating active electrode 32 from return electrode 34. Active electrode 32 is connected to a generator via an active conductor 38 which extends through the hollow centre of return electrode 34. Return electrode 34 is also a metallic shaft, which is partially covered by plastics insulation 40, such that an exposed region 42 of return electrode 34 is substantially at the distal end of electrode 34.

Figure 2:
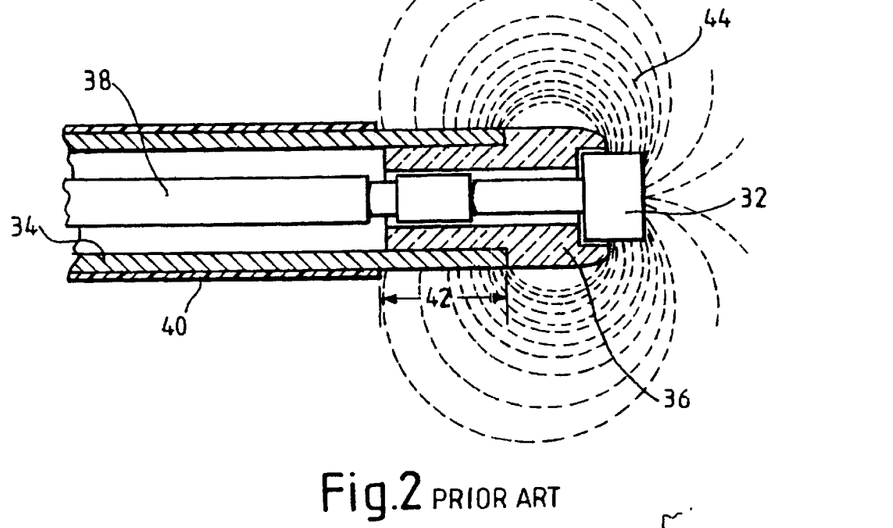
FIG. 2 is a partially sectioned side view of a prior art electrode assembly.

The shortest conduction path between the active electrode 32 and the return electrode 34 is in the region of 3 mm. However, due to the concentration of current at the distal end of the return electrode 34 as shown by the field pattern lines 44, increasing the size of the electrode (defined by termination of the shaft insulation 40) has little effect on the current density in that region.

The length over which conduction pathways extend proximally along the return zone in the electrode assembly of FIG. 1 is very different from that in the example shown in FIG. 2. In FIG. 1 there is a shortest conduction path of 3 mm and a longest of 23 mm between the return zone 24 and active zone 20, as compared to 3 mm and 6.3 mm between the proximal end of the active electrode 32 and the distal and proximal ends of the return electrode 34, respectively. It will be noted from the varying spacing of the field pattern lines 44 that the current density from one end of the return to the other in the prior art example of FIG. 2 changes considerably.

In the preferred embodiment of FIG. 1, this varying current density causes a varying voltage drop across the dielectric coating 22 to the extent that they are interactive. Where current density tends to be high, the voltage drop across the coating 22 is also high and, conversely, low current density causes a low voltage drop. Thus, the dielectric coating 22 interacts with current so that areas of high current density are reduced and the electric field 26 is more uniformly distributed over a zone of the electrode, the return zone 24. The higher the coating impedance by virtue of thickness or lower output frequency, the more even the current density and the larger is its area of distribution over the return electrode. . This has a significant effect on the electric field 26 produced by the electrode assembly 10 when the active zone 20 is in the uncoated or wetted state. The size of the electric field 26 influences the depth of penetration of the electrosurgical effect into a tissue structure which, with the active zone 20 uncoated or in the wetted state, results in desiccation, coagulation or thermal modification of the tissues.

The exposed conductive return region 42 of the prior art electrode assembly 30 shown in FIG. 2 provides no such current density limit. Consequently, there are high current densities at the front edge of exposed region 42 of return electrode 34, which can cause tissue damage if the exposed region 42 is brought into intimate contact with tissue. These high current densities occur even if the length of return electrode exposed region 42 is increased.

A coated return that limits current density, such as return zone 24 shown in FIG. 1, can, therefore, be constructed with a larger effective area to disperse current and reduce the propensity for the return to cause tissue damage. Additionally, the limited current density is such that the effects of carbon tracking between the active and return zones, such as zones 20 and 24 of FIG. 1, are virtually eliminated.

An additional desirable effect of limiting current density is that the electric field pattern created by the electrode assembly enlarges and becomes more even. Significantly, this enlarged field pattern only occurs in high current situations. Tissue desiccation occurs when the active electrode is wetted, and the impedance is lowest and, therefore, current is the highest. The enlarged field pattern in these circumstances ensures greater current flow in the tissue, and, therefore, increases the desiccation effect for a given power.

Figure 3:
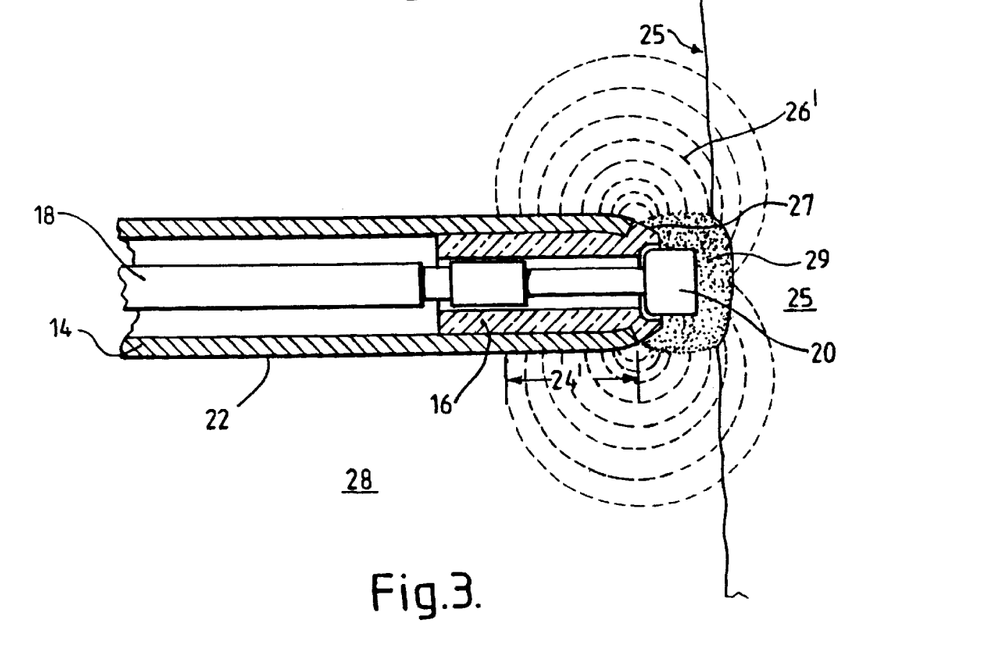
FIG. 3 is a partially sectioned side view of the electrode assembly of a second preferred embodiment of the invention.

Referring now to FIG. 3, a modified form of the electrode assembly of FIG. 1 has an active electrode 12 used for vaporisation, with the separation from the return zone being 1 mm or less. In this case, it is desirable that the field pattern 26' is small so as not to create excessive thermal damage. When used for vaporisation, there is a dramatic load impedance increase of 20 times, maybe up to 50 times, that of the load impedance seen during desiccation. Typically, there is also a decreased power requirement to about 50%. The current can, therefore, fall to 10% of its original value. The voltage drop across the coating 22, therefore, decreases by 90%, and the electric field pattern 26' collapses as a result of the low current densities, as shown in the example of FIG. 3. This is highly advantageous because it then minimises the depth of thermal effect. The effective area of the return zone 24' therefore dynamically changes in the different output modes as well as being a function of the properties of the dielectric material 22 and the electrosurgical output frequency.

A small field pattern, such as that shown in FIG. 3, during tissue vaporisation is desirable because heating of the saline 28 other than close to the electrode assembly is undesirable. Prior art electrode configurations would normally be limited to a minimum conductive path length to prevent potential breakdowns occurring over the insulator separating the exposed active and return electrodes. Thus, in exposed electrode designs, there is a minimum sized field pattern defined by the minimum conductive path length. Typically, therefore, the conductive pathway of an exposed electrode configuration, such as that shown in FIG. 2, extends beyond the field of vaporisation to avoid direct arcing between the two electrodes 32 and 34, which inevitably results in some collateral thermal effects beyond the margin of tissue removal.

If, however, one or other or both return and active zones 24' and 20 are coated with low loss dielectric material, it is possible for the electrode separation zone 27 to fall within the field of vaporisation 29, as shown in FIG. 3. Electrical discharge may still occur directly between the regions of the return and active zones 24' and 20 within the vapour pocket 29, but, due to there being no surface charge on the dielectric coating 22, these are low energy discharges with the high energy discharges still preferentially occurring to the tissue surface 25. Thermal dissipation from electrode assembly 10 to surrounding saline, tissue or carbon residues is significantly reduced.

The lower the capacitance between the dielectric coated return to the conductive fluid, the higher is the voltage of the return electrode with respect to the patient potential. As explained above, this voltage drop is advantageous in terms of the effects. Capacitive coupling to other instruments or to tissue at the entry point of the electrode assembly to the body cavity can be prevented by enclosing the shaft proximally of the return zone in a thicker low permitivity dielectric, as shown in FIG. 4, or by electrically isolating the tip of the electrode assembly, i.e. including the return electrode, by means of an in-line choke or isolation transformer, as shown in FIG. 5.

Figure 4:
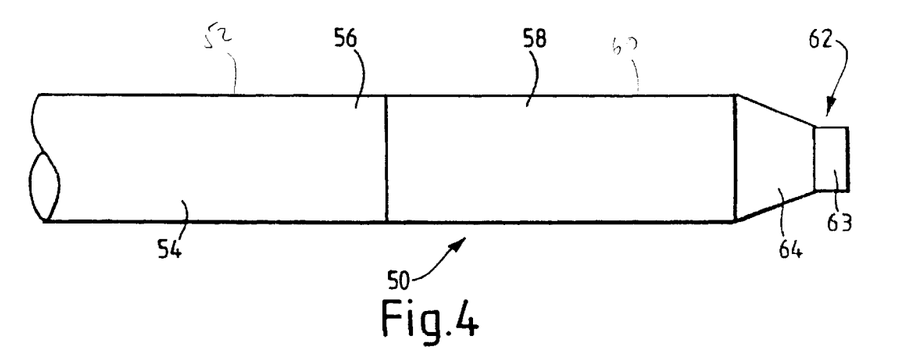
FIG. 4 is a side view of an electrode assembly having a dielectric coating with different dielectric permitivities in order to define a return zone.

Referring to FIG. 4, an electrode assembly 50 has a thicker dielectric coating 52 of relatively low permittivity applied over a region 54 of a return electrode shaft 56 proximal to a return zone 58 defined by an area of thinner dielectric coating 60 of relatively high permittivity to yield capacitance per unit area to surrounding conductive fluid which is lower than that in the return zone. The electrode assembly 50 shown in FIG. 4 also includes an active electrode 62 with an active zone 63 that is separated from return electrode 56 by an insulator 64. The dielectric arrangement shown in FIG. 4 further reduces current densities to levels sufficient to prevent tissue damage when in contact with the proximal region 54 of the shaft 56. This arrangement does not, however, prevent capacitive coupling of some energy into a metal object. Such coupling is most likely to occur when the electrode assembly 50 is introduced to the operative site through a metallic channel such as the working channel of an endoscope (not shown). In these circumstances it may be preferable to use one or other of the solutions described with reference to FIGS. 5A and 5B.

Figure 5A:
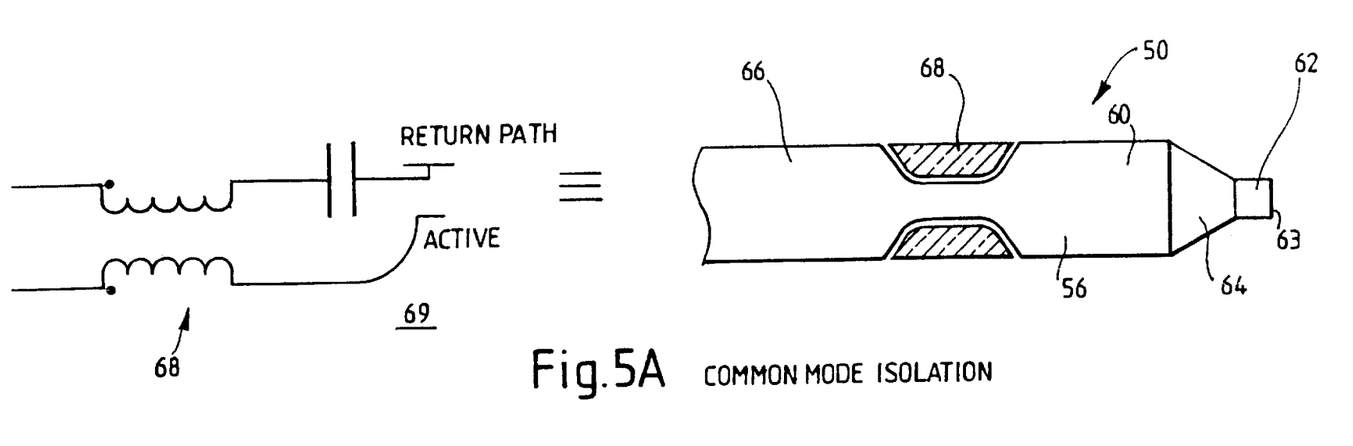
FIGS. 5A and 5B are partially sectioned side views and equivalent circuits of further electrode assemblies showing additional techniques for defining a return zone.
Figure 5B:
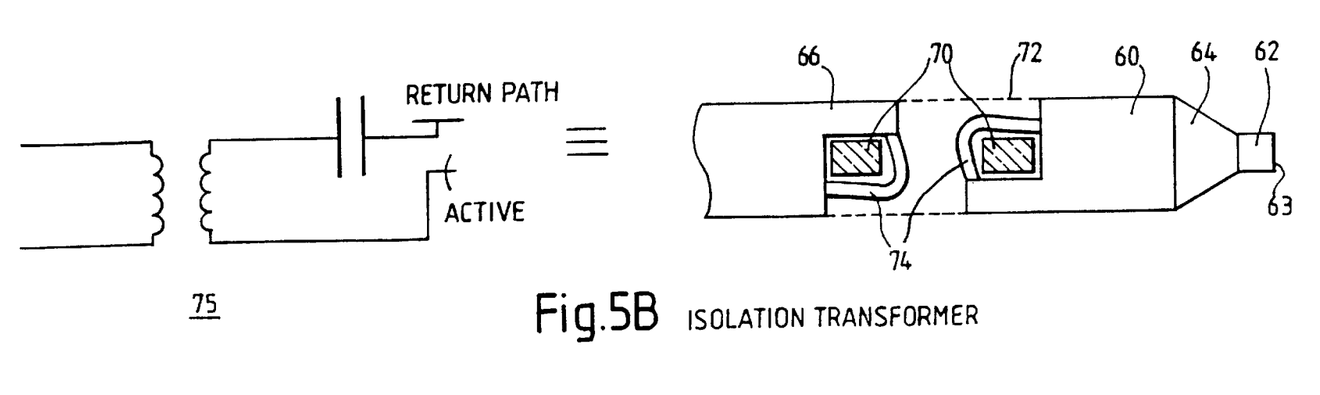

The elevated potential of return electrode 56 can be isolated to the distal end of electrode assembly 50 by using a common mode choke 68 (FIG. 5A) or an isolating transformer 70 (FIG. 5B). The common mode isolation arrangement of FIG. 5A is probably the simpler of the two to realise, since the common mode choke can be constructed as a ferrite toroid or toroidal sleeve 68 around the electrode shaft 56, and, therefore, involves no wound components. For example, a high permeability material can be used to construct a toroidal sleeve with a current-area product AI of 2 $\mu$H or more. At 40.68MHz this provides an isolation impedance of 500$\Omega$. The potential of isolated shaft 66 with respect to ground is negligible. The return zone 60 is defined by that portion of the insulated shaft distal of the choke 68 which with the active zone 63 is then free to assume any potential with respect to ground. A schematic 69 of the choke arrangement is also shown in FIG. 5A. The same outcome provided by the choke arrangement of FIG. 5A is also provided by the transformer arrangement of FIG. 5B, wherein the high permeability ferrite toroid 70 is utilised as an isolation transformer mounted in a supporting insulator member 72 and including at least single turn windings 74 each in the form of, for instance, a single turn linking the inner active conductor to the surrounding return conductor (forming a coaxial sheath as in the embodiments described above). The proximal isolated shaft 66 is then isolated from the potential developed in the return zone 60 distally of the transformer arrangement. A schematic 75 of the transformer arrangement is also shown in FIG. 5B.

Figure 6A:
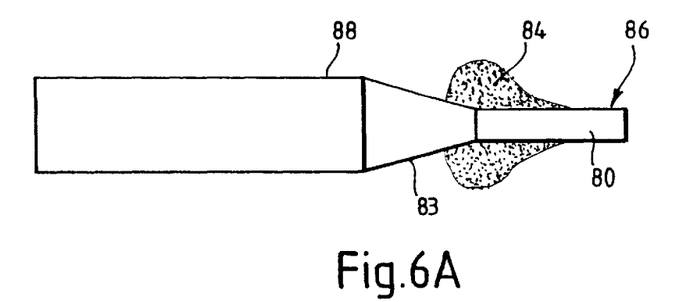
FIGS. 6A and 6B are side views of two further electrode assemblies for instruments in accordance with the invention.
Figure 6B:
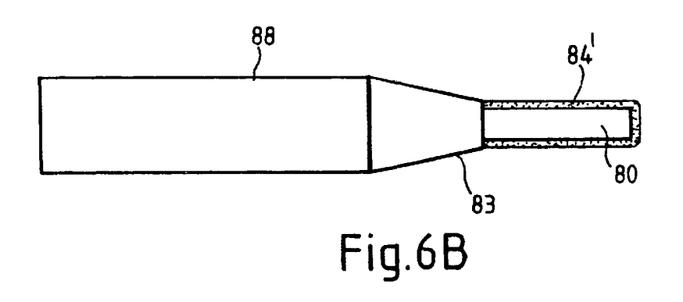

In prior art devices, the area of the active electrode is invariably less than that of the return electrode so as to promote increased power densities at the active electrode. Alternatively, other prior art strategies can be employed to define the active electrode despite the fact that the contact area is at least as large as the return electrode. These strategies are, however, ineffective when the active electrode is configured as a long needle or wire form (due to varying current densities) such as that depicted in FIG. 6A. A long thin active electrode 80, as shown in FIG. 6A, projecting from an insulator 83 can result in a condition where the most proximal portion is surrounded by a vapour pocket 84, yet the distal end 86 is still in the wetted state. This causes very high power demand due to the high voltage applied to sustain vaporisation simultaneously to a direct saline circuit path. To overcome this situation, the prior art makes use of various geometric limitations related to the longest and shortest conduction path lengths between the active electrode 80 and the most distally disposed edge of the return electrode 88. These limitations, in effect, define the length of the active electrode 80 relative to the current density distribution over the surface of such electrode. Dielectric coating of the active electrode 80 prevents this condition, as shown in FIG. 6B.

A dielectric coating 90 on the long active electrode 80 has similar effects to that of dielectric coating the return electrode 88, but also has some additional beneficial effects. The fact that the active surface is current density limiting prevents the undesirable effects shown in FIG. 6A. The electrode assembly can also operate power-efficiently with the active electrode 80 only partly enveloped with a vapour pocket. This results in a lower power threshold to change from wetted to vaporisation states, since only a small amount of saline over the surface of the electrode has to be vaporised to reach a sustainable condition, whereas an exposed active electrode would have to be completely enveloped. The current density limiting also allows a voltage gradient to be established over the surface of the coated active electrode that reduces the voltage drop per unit treatment axis length through the saline. Thus, when in the vaporisation state, the vapour pocket 84'0 is more uniform in thickness, as shown in FIG. 6B.

The ability of the electrode to support vaporisation over only part of its length is also advantageous in adverse conditions, such as high flow environments. An exposed active electrode is vulnerable to these conditions because, if the vapour pocket is swept away from the side of the electrode, the whole vapour pocket is likely to collapse. Thus, coating a long active electrode with a dielectric allows the vapour pocket to operate efficiently over part of the active electrode and can operate to spread the vapour pocket to some extent over the active electrode.

Figure 7:
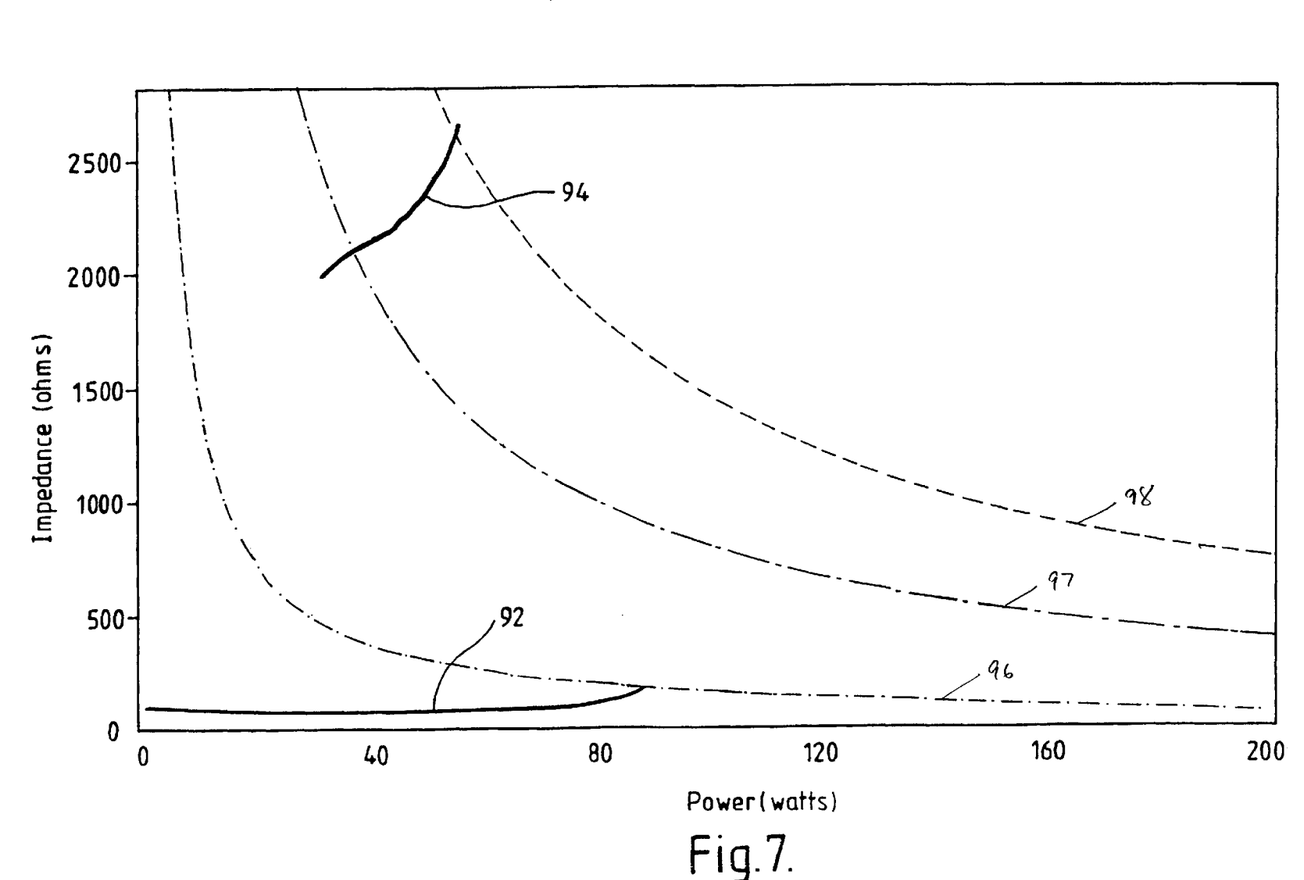
FIG. 7 is a graph of an impedance versus power relationship.

FIG. 7 shows the hysteresis in the load impedance versus applied power characteristic for an exposed electrode design in a low flow environment. When one or each electrode is coated, in accordance with the invention, a similar characteristic applies in respect of the conductive path between any point on the outer surface of the coating in one electrode to the outer surface of the other electrode (or, if coated, the outer surface of its coating). The two bold traces show the operating characteristics in the wetted state 92 (the lower trace) and in the vaporisation state 94 (the upper trace). The constant voltage lines 96, 97, 98 represent desiccate, low vaporise and high vaporise voltage respectively. With an exposed active electrode as in FIG. 6A, there can be only one voltage over the surface of the active electrode due to the conductive nature of the metallic material. This is not true, however, for a coated active electrode as in FIG. 6B. It is possible for one area of the electrode to behave in the wetted state while the other is in vaporisation state. This is possible on a very small scale. A bubble over the surface of the active electrode defines a vaporisation state over the area of the bubble. Thus, when high flow rates are used, the low impedance created on one side of the active electrode quenches the vaporisation state of an uncoated electrode but only partially quenches a coated electrode (i.e., that part most exposed to flow). Instead of considering a single hysteresis diagram for the electrode, the behaviour of a coated electrode is more appropriately modelled by an infinite number of hysteresis diagrams that are virtually independent.

A unique advantage of the capacitively coupled non-contact active electrode described above is the lack of nerve stimulation. When a metal electrode is used for tissue cutting or vaporisation, there is significant nerve stimulation. It is thought that this stimulation arises due to thermionic rectification as a result of the active electrode being heated by arcing. A dielectric coating as described above prevents electron emission and consequently the thermionic effect. Peak currents drawn by arcs are also reduced by virtue of the surface capacitance of the coating.

The coating on the active zone has to withstand both high temperatures and large temperature gradients. Ceramics are materials capable of withstanding this. Similar design factors are employed such as ensuring high dielectric constants and low coating thickness. There are many materials to chose from with relative dielectric constants as high as 100 (titanium dioxide) or 1600 ($BaTiO_3$) to materials of dielectric strength up to 50 kV/mm (quartz, ruby or aluminium nitride).

There are many viable manufacturing techniques such as hollow cavity forms of ceramic with internally inked and fired metallization or plasma sprayed/vapour deposited ceramic on a metal substrate with laser glazing. Coating processes provide the minimum thickness which is in the region of 0.03 mm. The tissue treatment area of the electrode of FIG. 1 is in the region of 10 $mm^2$. If this is coated with alumina, the relative dielectric constant is 10. The coupling capacitance is therefore 27 pF for alumina or 270 pF for titanium dioxide.

Figure 8:
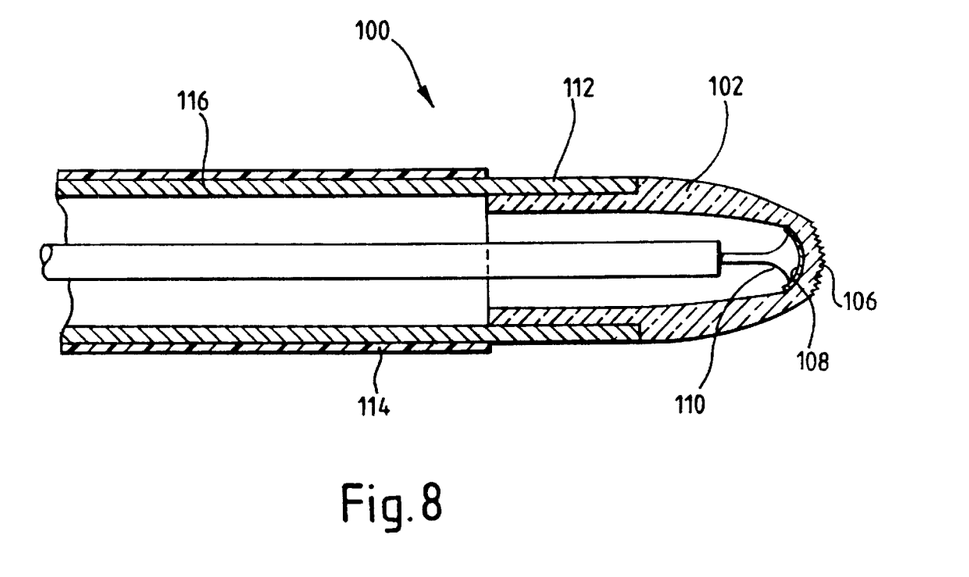
FIG. 8 is a partially sectioned side view of a further preferred electrode assembly, the features of which may be combined with the features of any of the other illustrated embodiments.

Cavity forms using ceramics are only really viable with high dielectric constant materials. Such a form is illustrated in FIG. 8. The electrode assembly 100 shown in FIG. 8 includes a hollow ceramic component 102 of thin cross-section. Ceramic nose component 102 has a textured distal end surface 106 which defines the active zone for improved tissue engagement. The internal surface of active zone 106 is coated with a metallised conductive metal layer 108 which is connected by active connection 110 to one output of the electrosurgical generator (not shown). In this example, the return zone 112 is a conductive return with the plastics shaft insulation 114 terminating proximally of the most distal part of the return shaft 116 of the instrument. Alternatively, the return zone 112 may also be coated with a dielectric material (not shown) so that both the active and return zones 106 and 112 are insulated from the tissue/fluid environment, this being one embodiment wherein all of the above cited advantages may be realised. In providing such an embodiment, the variables of dielectric impedance of both the active zone 106 and return zone 112 must be summated in order to establish the required operating frequency of the electrosurgical generator.

Advantageously, when utilising an embodiment wherein both the active and return zones are insulated by a dielectric material, the dielectric coating of the active can be designed to be imperfect. Dielectric losses at the active surface promote local heating and reduce the power requirement to reach the vaporisation state. Another attraction of this technique is that when vaporisation is attained and the ceramic is subjected to large thermal stress, the dielectric losses are reduced due to the increase in load impedance and the consequent drop in current. $BaTiO_3$ provides such a lossy dielectric for this application. Other manipulations of the dielectric properties may be advantageous in optimising performance particularly as it relates to the combined dynamic interaction of electrosurgical output mode, output frequency, dielectric properties related to these variables and dielectric temperature.

At normal electrosurgical frequencies, the clinical effects can be attributed entirely to conduction. At higher frequencies, however, dielectric effects of the load have a significant effect. For example, while normal saline (0.9% W/V) has a conductivity of 15.1 mS, it has a relative dielectric constant of approximately 100 at the frequencies of interest. At 40.68 MHz there is, therefore, a capacitive impedance of 440 $\Omega$/cm and a resistive one of 66 $\Omega$cm. The capacitive effect within the saline is minimal. However, the major difference is in the electrical behaviour of the target tissue. Cartilage, for example, has a poor conductivity of about 1.5 to 2 ms, yet has a similar dielectric constant. Consequently, VHF currents in cartilage are approximately twice those obtained at low frequencies conventially used in electrosurgery, due to dielectric effects. The conductive properties of any high impedance tissue are similarly doubled and thus tissue effects are enhanced.

In summary, significant features of the systems described above include an electrode assembly having at least an active zone for application to the target site and return zone, one or both of the zones being coated with a dielectric material and immersed in a a conductive fluid such that the electrosurgical circuit is completed by capacitive coupling between one or both of the zones and the fluid used to irrigate or distend the operative site. The active zone may be used to vaporise, coagulate, desiccate or thermally modify bodily tissues immersed in the fluid.

The electric field pattern created between the active and return zones of electrode assembly is manipulated using a combination of the dielectric coating thickness for a given dielectric constant, employing a coating material with a variable dielectric constant at different temperatures, and selecting the size and geometry of the return zone of the electrode assembly and the output frequency of the electrosurgical generator.

Uniform current density is provided over the surface of the active zone of the electrode assembly to support and sustain the formation of a partial vapour pocket over one or more sections of the active zone, and wherein the proximity of the return zone to the active zone has minimal influence over the distribution and size of the vapour pocket formed over at least a part of the active zone and further minimises the propensity for collapse of the entire vapour pocket or pockets when the active zone is exposed to a flow of fluid.

Current densities are reduced over one or both of the active and return zones of the electrode assembly such that the currents necessary to elevate the temperature of a carbon track cannot be developed. A further advantage of a wider distribution of current densities over the active and return zones is that the electrosurgical output can only be supported when substantially all of the electrode assembly is immersed, thereby eliminating the overheating encountered during partial immersion of prior art electrode structures.

Such properties may be realised by combination of instruments, application of the specified surgical techniques and identification of such combinations as may be required to apply the invention to different anatomical situations to provide vaporisation, coagulation, desiccation, or to otherwise thermally modify tissue structures.

The foregoing description of preferred embodiments of the invention has been presented for purposes of illustration and description. It is not intended to be exhaustive or to limit the invention to the precise form disclosed, and obviously many modifications, variations and methods of application are possible from the teachings of the examples herein given. The embodiments were chosen to best explain the principles of the invention as they apply to different situations of use and thereby to enable others skilled in the art to best utilise the invention including any modifications as may be necessary to practise additional aspects of use contemplated as a result of this disclosure. It is intended that the scope of the invention be defined by the claims appended hereto.

For the purposes of the law relating to permissible amendments of the present application, it should be noted that, whilst the particular arrangement of the following claims has been prepared with a view to presenting essential and preferred features of the invention in a logical and concise way, we hereby specifically include as part of the content of this application as filed all possible combinations of the individual features contained in the claims or the preceding description, i.e. in addition to presently recited combinations.

What is claimed is:

1. An electrosurgery system for treating tissue immersed in an electrically conductive fluid, comprising:
    a generator for delivering a radio frequency tissue treatment output in the frequency range of from 100 kHz to 50 MHz, and
    an elongate instrument shaft configured to be mounted at a proximal end to a handpiece and carrying at its distal end a bipolar electrode assembly connected to the generator, wherein the electrode assembly includes:
    an active electrode with an active zone at a distal end of the active electrode; and
    a return electrode with a return zone near the active zone;
    wherein at least one of the active and return zones has an electrically insulating dielectric covering such that in use a radio frequency electrical circuit between the active and return electrodes through the conductive fluid is completed primarily by dielectric coupling through the dielectric covering.

2. A system according to claim 1, wherein the return zone is adjacent and set back from the active zone in the proximal direction.

3. A system according to claim 1, wherein the insulating covering encases the return zone, and the active zone is exposed.

4. A system according to claim 1, wherein the frequency of operation of the generator and the construction of the electrode assembly are such that when a radio frequency current of 2 amps is delivered to the electrode assembly when immersed in normal saline, the current density at the outer surface of the dielectric covering does not exceed 50 mA/mm$^2$.

5. A system according to claim 1, wherein the frequency of operation of the generator and the construction of the electrode assembly are such that application of radio frequency power by the generator to the electrode assembly results in a substantially uniform distribution of electric field over said return zone and a corresponding substantially uniform current density of said electric field.

6. A system according to claim 1, wherein both the active zone and the return zone are encased in respective insulative dielectric coverings so that said active zone is insulated from direct electrical contact with said tissue and said electrically conductive fluid and, in use, a circuit is completed between said active and return electrodes primarily by dielectric coupling through both coverings.

7. A system according to claim 6, wherein the frequency of operation of the generator and the construction of the electrode assembly are such that there is a substantially uniformly distribution of electric field over said active and return zones and a corresponding substantially uniform current density of said electric field.

8. A system as recited in claim 7, wherein said dielectric coverings over said return zone and said active zone both have a thickness less than 50 lm.

9. A system according to claim 6, wherein said dielectric coverings over said return zone and said active zone both have a thickness greater than 50 lm.

10. A system according to claim 1, wherein the material of each dielectric covering is a low loss dielectric material.

11. A system according to claim 1, wherein each dielectric covering has a thickness greater than 50 lm.

12. A system according to claim 1, wherein each said dielectric covering is of sufficient thickness to result in a limited current density over said active and return zones so as to prevent significant power dissipation in any carbon tracking between said active and return zones during use of said electrode assembly.

13. A system according to claim 1, wherein the insulating covering which covers the return zone has a first pre-determined thickness and wherein a remainder of the return electrode is coated with a second dielectric covering having a second pre-determined thickness greater than the first pre-determined thickness and capable of substantially preventing capacitive coupling of the said remainder of the return electrode to other instruments or to tissue within a body cavity.

14. A system according to claim 13, wherein the return zone is isolated from the remainder of the return electrode by an isolating transformer positioned between the return zone and the remainder of the return electrode.

15. A system according to claim 13, wherein the return zone is isolated from the said remainder of the return electrode by an isolating transformer positioned between the return zone and the said remainder of the return electrode.

16. A system according to claim 1, wherein both the active zone and the return zone are encased in respective insulative dielectric coverings, wherein the dielectric covering encasing the return zone has a first pre-determined thickness and wherein a remainder of the return electrode is coated with a third dielectric insulating material layer having a second pre-determined thickness greater than the first pre-determined thickness and capable of substantially preventing capacitive coupling of the said remainder of the return electrode to other instruments or to tissue within a body cavity.

17. A system according to claim 16, wherein the return zone is isolated from the said remainder of the return electrode by a common mode choke positioned between the return zone and the said remainder of the return electrode.

18. A system according to claim 16, wherein the return zone is isolated from the said remainder of the return electrode by an isolating transformer positioned between the return zone and the remainder of the return electrode.

19. A system according to claim 1, wherein the insulative covering encases the active zone.

20. A system according to claim 19, wherein the frequency of operation of the generator and the construction of the electrode assembly are such that when a radio frequency current of 2 amps is delivered to the electrode assembly when immersed in normal saline, the current density at the outer surface of the dielectric covering does not exceed 50 mA/mm$^2$.

21. A system according to claim 19 or claim 20, wherein the active electrode is configured as at least one of a long needle and a wire and wherein the insulating covering on the active zone is of sufficient thickness that current density is limited over the active zone and the active electrode can operate power efficiently when partly enveloped within a vapour pocket during vaporisation.

22. An electrosurgical instrument for treating tissue immersed in an electrically conductive fluid with radio frequency energy in the frequency range of from 100 kHz to 50 Mhz, wherein the instrument comprises an elongate shaft configured to be mounted at a proximal end to a handpiece and carrying at its distal end a bipolar electrode assembly which includes:
  an active electrode with an active zone at a distal end of the active electrode; and
  a return electrode with a return zone near the active zone;
  wherein at least one of the active and return zones has an electrically insulating dielectric covering such that in use a radio frequency electrical circuit between the active and return electrodes through the conductive fluid is completed at least primarily by dielectric coupling through the dielectric covering.

23. An instrument according to claim 22, wherein the return zone is adjacent and set back from the active zone in the proximal direction.

24. An instrument according to claim 22, wherein the insulating covering encases the return zone, and the active zone is exposed.

25. An instrument according to claim 24, wherein said dielectric covering which covers the return zone has a first pre-determined thickness and wherein a remainder of the return electrode is coated with a second dielectric covering having a second pre-determined thickness greater than the first pre-determined thickness and capable of substantially preventing capacitive coupling of said remainder of the return electrode to other instruments or to tissue within a body cavity.

26. An instrument according to claim 25, wherein the return zone is isolated from said remainder of the return electrode by a common mode choke positioned between the return zone and said remainder of the return electrode.

27. An instrument according to claim 25, wherein the return zone is isolated from said remainder of the return electrode by an isolating transformer positioned between the return zone and said remainder of the return electrode.

28. An instrument according to claim 22, wherein the electrode assembly is constructed such that, when an electrosurgical radio frequency current at at least one frequency in the said frequency range is delivered to the assembly when immersed in normal saline, the current density at the outer surface of the dielectric covering does not exceed 50 mA/mm$^2$.

29. An instrument according to claim 22, wherein the thickness of the or each dielectric covering is greater than 50:m.

30. An instrument according to claim 22, wherein the thickness of the or each dielectric covering is less than 50:m.

31. An instrument according to claim 22, wherein both the active zone and the return zone are encased in respective insulative dielectric coverings, wherein the dielectric covering encasing the return zone has a first pre-determined thickness and wherein a remainder of the return electrode is coated with a third dielectric insulating material layer having a second pre-determined thickness greater than the first pre-determined thickness and capable of substantially preventing capacitive coupling of said remainder of the return electrode to other instruments or to tissue within a body cavity.

32. An instrument according to claim 22, wherein the dielectric covering encases the active zone.

33. An instrument according to claim 32, wherein the active electrode is configured as a long needle or wire and wherein the insulating covering on the active zone is of sufficient thickness that current density is limited over the active zone and the active electrode can operate power efficiently when partly enveloped within a vapour pocket during vaporisation.

34. An instrument according to claim 32, wherein the active electrode comprises a ceramic body defining an internal cavity which cavity is lined with metal, the ceramic body having an outer tissue or fluid contact surface.

35. An instrument according to claim 32, wherein the return zone is covered with an insulative dielectric outer layer having an outer fluid contact surface.

36. An electrosurgical instrument for use at a frequency or frequencies in the range of from 100 kHz to 50 MHz, the instrument having a bipolar electrode assembly for tissue treatment when immersed in a conductive fluid, wherein the instrument comprises an elongate shaft mounted at one end to a handpiece, and carrying the electrode assembly at its other end, and wherein the electrode assembly comprises at least one distal active electrode, and an adjacent return electrode set back proximally of the active electrode, the return electrode being encased in an insulative dielectric layer.

37. A laparoscopic electrosurgical instrument for wet field electrosurgery, wherein the instrument comprises a tubular elongate shaft for insertion into a body cavity and, at the end of the shaft for insertion into the body cavity, an electrode assembly comprising a first conductor at an extreme distal end of the instrument and a second conductor insulated from the first conductor and set back from the distal end, wherein at least the second conductor is encased in an insulative outer dielectric layer.

38. An electrosurgical system for treating tissue structure contained within a body cavity and immersed in an electrically conductive fluid, said system comprising: a generator for delivering a radio frequency output for the treatment of tissue structures in the high to very high frequency range; and an electrode assembly connected to said generator, said electrode assembly comprising: an active electrode including an active zone at a distal end of said active electrode; a return electrode including a return zone defined by an electric field developed between said active electrode and said return electrode when said electrode assembly is connected to said radio frequency output of said generator; and an insulator separating said return electrode from said active electrode; said return zone being coated with a layer of dielectric insulating material wherein, in use, said return zone is insulated from direct electrical contact with said tissue and said electrically conductive fluid so that an electrical circuit is completed between said active and return zones by dielectric coupling through said dielectric insulating material.

39. An electrode assembly for treating tissue structure contained within a body cavity and immersed in an electrically conductive fluid, said electrode assembly being connected to a generator for delivering a radio frequency output for the treatment of tissue structures in the high to very high frequency range, said electrode assembly comprising: an active electrode including an active zone at a distal end of said active electrode;

a return electrode including a return zone defined by an electric field developed between said active electrode and said return electrode when electrode assembly is connected to said radio frequency output of said generator; and an insulator separating said return electrode from said active electrode;

said return zone being coated with a dielectric insulating material layer wherein, in use, said return zone is insulated from direct electrical contact with said tissue and said electrically conductive fluid so that an electrical circuit is completed between said active and return zones by dielectric coupling through said dielectric insulating material.

40. An electrode assembly for treating tissue structure contained within a body cavity and immersed in an electrically conductive fluid, said electrode assembly being connected to a generator for delivering a radio frequency output to said electrode assembly, said electrode assembly comprising:

an active electrode in the form of a ceramic cavity lined internally with metal, said active electrode including an active zone at a distal end of said active electrode; and a return electrode including a return zone defined by an electric field developed between said active electrode and said return electrode when said electrode is connected to said radio frequency output of said generator;

said ceramic cavity being a dielectric insulating material, wherein, in use, an electrical circuit is completed between said active and return zones by dielectric coupling.

* * * * *

UNITED STATES PATENT AND TRADEMARK OFFICE
CERTIFICATE OF CORRECTION

PATENT NO. : 6,758,846 B2
DATED : July 6, 2004
INVENTOR(S) : Goble et al.

It is certified that error appears in the above-identified patent and that said Letters Patent is hereby corrected as shown below:

Column 15,
Line 59, change "at least one" to -- both --.

Column 17,
Line 41, change "at least one" to -- both --.

Column 18,
Line 51, before "return", insert -- active and --, and change "electrode" to -- electrodes --.
Line 60, change "at least the second conductor is" to -- the first and second conductors are --.

Column 19,
Line 10, change "said return zone" to -- both zones --.

Column 20,
Line 3, change "said return zone" to -- both zones --.

Signed and Sealed this

Sixteenth Day of August, 2005

JON W. DUDAS
*Director of the United States Patent and Trademark Office*